United States Patent
Christman et al.

(10) Patent No.: US 8,369,961 B2
(45) Date of Patent: Feb. 5, 2013

(54) MULTI-ANTENNA FOR AN IMPLANTABLE MEDICAL DEVICE

(75) Inventors: Timothy J. Christman, Woodbury, MN (US); Jason J. Edwardson, Wyoming, MN (US); Bart A. Carey, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 529 days.

(21) Appl. No.: 12/565,482

(22) Filed: Sep. 23, 2009

(65) Prior Publication Data

US 2010/0016925 A1    Jan. 21, 2010

Related U.S. Application Data

(63) Continuation of application No. 11/423,262, filed on Jun. 9, 2006, now Pat. No. 7,613,522.

(51) Int. Cl.
*A61N 1/08* (2006.01)

(52) U.S. Cl. .......... 607/60; 607/1; 607/2; 607/32; 607/36; 607/115; 607/116; 343/718; 343/845; 343/872; 343/873

(58) Field of Classification Search .......... 607/1–2, 607/32, 36, 60, 115–116; 343/718, 845, 343/872–873
See application file for complete search history.

(56) References Cited

U.S. PATENT DOCUMENTS

| | | |
|---|---|---|
| 3,667,477 A | 6/1972 | Susset et al. |
| 3,718,909 A | 2/1973 | Greatbatch |
| 3,830,242 A | 8/1974 | Greatbatch |
| 4,230,128 A | 10/1980 | Aramayo |
| 4,262,632 A | 4/1981 | Hanton et al. |
| 4,341,982 A | 7/1982 | Lahti et al. |
| 4,441,498 A | 4/1984 | Nordling |
| 4,519,401 A | 5/1985 | Ko et al. |
| 4,542,535 A | 9/1985 | Bates et al. |
| 4,556,063 A | 12/1985 | Thompson et al. |
| 4,562,841 A | 1/1986 | Brockway et al. |
| 4,580,950 A | 4/1986 | Sumikawa et al. |

(Continued)

FOREIGN PATENT DOCUMENTS

| | | |
|---|---|---|
| EP | 0168640 A2 | 1/1986 |
| EP | 1050265 A2 | 11/2000 |

(Continued)

OTHER PUBLICATIONS

"U.S. Appl. No. 09/798,249, Non-Final Office Action mailed Mar. 28, 2003", 7 pgs.

(Continued)

*Primary Examiner* — Carl H Layno
*Assistant Examiner* — Deborah Malamud
(74) *Attorney, Agent, or Firm* — Schwegman Lundberg & Woessner, P.A.

(57) ABSTRACT

A system for enabling telemetry in implantable medical devices is provided. An implantable medical device has radio-frequency telemetry capabilities. The device includes a housing and electronic circuitry contained within the housing. The device also includes an array of antennas connected to the electronic circuitry. According to various embodiments, the array and circuitry are adapted to facilitate far-field transmission and reception of modulated radio-frequency energy at one or more specified carrier frequencies. Individual antenna elements in the array are connected simultaneously or in a mutually exclusive manner to electronic circuitry, according to various embodiments. Individual antenna element geometries are sized to optimize individual antennas each for a different range of operating frequencies, according to various embodiments. Other aspects and embodiments are provided herein.

10 Claims, 5 Drawing Sheets

U.S. PATENT DOCUMENTS

| | | | |
|---|---|---|---|
| 4,634,294 A | 1/1987 | Christol et al. |
| 4,803,987 A | 2/1989 | Calfee et al. |
| 4,944,299 A | 7/1990 | Silvian |
| 5,025,808 A | 6/1991 | Hafner |
| 5,058,581 A | 10/1991 | Silvian |
| 5,089,019 A | 2/1992 | Grandjean |
| 5,109,853 A | 5/1992 | Taicher et al. |
| 5,113,869 A | 5/1992 | Nappholz et al. |
| 5,118,825 A | 6/1992 | Wu |
| 5,127,404 A | 7/1992 | Wyborny et al. |
| 5,314,453 A | 5/1994 | Jeutter |
| 5,336,245 A | 8/1994 | Adams et al. |
| 5,337,756 A | 8/1994 | Barbier et al. |
| 5,342,408 A | 8/1994 | deCoriolis et al. |
| 5,385,578 A | 1/1995 | Bush et al. |
| 5,486,200 A | 1/1996 | Lindemans |
| 5,516,285 A | 5/1996 | Yacker et al. |
| 5,534,019 A | 7/1996 | Paspa |
| 5,535,752 A | 7/1996 | Halperin et al. |
| 5,556,421 A | 9/1996 | Prutchi et al. |
| 5,562,713 A | 10/1996 | Silvian |
| 5,579,876 A | 12/1996 | Adrian et al. |
| 5,593,430 A | 1/1997 | Renger |
| 5,598,847 A | 2/1997 | Renger |
| 5,650,759 A | 7/1997 | Hittman et al. |
| 5,683,432 A | 11/1997 | Goedeke et al. |
| 5,697,958 A | 12/1997 | Paul et al. |
| 5,735,887 A | 4/1998 | Barreras, Sr. et al. |
| 5,749,912 A | 5/1998 | Zhang et al. |
| 5,766,232 A | 6/1998 | Grevious et al. |
| 5,784,032 A | 7/1998 | Johnston et al. |
| 5,807,397 A | 9/1998 | Barreras |
| 5,833,603 A | 11/1998 | Kovacs et al. |
| 5,861,019 A | 1/1999 | Sun et al. |
| 5,862,803 A | 1/1999 | Besson et al. |
| 5,876,331 A | 3/1999 | Wu |
| 5,904,708 A | 5/1999 | Goedeke |
| 5,919,210 A | 7/1999 | Lurie et al. |
| 5,957,854 A | 9/1999 | Besson et al. |
| 5,958,645 A | 9/1999 | Hirose et al. |
| 6,009,350 A | 12/1999 | Renken |
| 6,115,583 A | 9/2000 | Brummer et al. |
| 6,115,634 A | 9/2000 | Donders et al. |
| 6,115,636 A | 9/2000 | Ryan |
| 6,116,636 A | 9/2000 | Bianchi Bazzi |
| 6,169,925 B1 | 1/2001 | Villaseca et al. |
| 6,205,358 B1 | 3/2001 | Haeg et al. |
| 6,240,317 B1 | 5/2001 | Villaseca et al. |
| 6,263,246 B1 | 7/2001 | Goedeke et al. |
| 6,275,737 B1 | 8/2001 | Mann |
| 6,309,350 B1 | 10/2001 | VanTassel et al. |
| 6,329,920 B1 | 12/2001 | Morrison et al. |
| 6,388,628 B1 | 5/2002 | Dettloff et al. |
| 6,392,610 B1 | 5/2002 | Braun et al. |
| 6,416,471 B1 | 7/2002 | Kumar et al. |
| 6,427,088 B1 | 7/2002 | Bowman, IV et al. |
| 6,434,429 B1 | 8/2002 | Kraus et al. |
| 6,456,256 B1 | 9/2002 | Amundson et al. |
| 6,470,215 B1 | 10/2002 | Kraus et al. |
| 6,505,072 B1 | 1/2003 | Linder et al. |
| 6,505,077 B1 | 1/2003 | Kast et al. |
| 6,531,982 B1 | 3/2003 | White et al. |
| 6,535,766 B1 | 3/2003 | Thompson et al. |
| 6,561,975 B1 | 5/2003 | Pool et al. |
| 6,574,508 B2 | 6/2003 | Zaouali et al. |
| 6,574,509 B1 | 6/2003 | Kraus et al. |
| 6,574,510 B2 | 6/2003 | Von Arx et al. |
| 6,592,518 B2 | 7/2003 | Denker et al. |
| 6,614,406 B2 | 9/2003 | Amundson et al. |
| 6,622,043 B1 | 9/2003 | Kraus et al. |
| 6,675,045 B2 | 1/2004 | Mass et al. |
| 6,687,546 B2 | 2/2004 | Lebel et al. |
| 6,708,065 B2 | 3/2004 | Von Arx et al. |
| 6,721,602 B2 | 4/2004 | Engmark et al. |
| 6,766,200 B2 | 7/2004 | Cox |
| 6,804,561 B2 | 10/2004 | Stover |
| 6,809,701 B2 | 10/2004 | Amundson et al. |
| 6,868,288 B2 | 3/2005 | Thompson |
| 7,016,733 B2 | 3/2006 | Dublin et al. |
| 7,072,718 B2 * | 7/2006 | Von Arx et al. ............... 607/60 |
| 7,103,413 B2 | 9/2006 | Swanson et al. |
| 7,149,578 B2 | 12/2006 | Edvardsson |
| 7,289,855 B2 | 10/2007 | Nghiem et al. |
| 7,309,262 B2 | 12/2007 | Zart et al. |
| 7,313,441 B2 | 12/2007 | Mass et al. |
| 7,317,946 B2 | 1/2008 | Twetan et al. |
| 7,319,901 B2 | 1/2008 | Dublin et al. |
| 7,363,087 B2 | 4/2008 | Nghiem et al. |
| 7,483,752 B2 | 1/2009 | Von Arx et al. |
| 7,613,522 B2 | 11/2009 | Christman et al. |
| 7,720,544 B2 | 5/2010 | Christman et al. |
| 7,848,788 B2 | 12/2010 | Tulley et al. |
| 2001/0034543 A1 | 10/2001 | Haeg |
| 2001/0047125 A1 | 11/2001 | Quy |
| 2002/0037756 A1 | 3/2002 | Jacobs et al. |
| 2002/0045920 A1 | 4/2002 | Thompson |
| 2002/0065539 A1 | 5/2002 | Von Arx et al. |
| 2002/0095195 A1 | 7/2002 | Mass et al. |
| 2002/0123776 A1 | 9/2002 | Von Arx et al. |
| 2003/0023175 A1 | 1/2003 | Arzbaecher et al. |
| 2003/0025645 A1 | 2/2003 | Amundson et al. |
| 2003/0028902 A1 | 2/2003 | Cubley et al. |
| 2003/0040779 A1 | 2/2003 | Engmark et al. |
| 2003/0083719 A1 | 5/2003 | Shankar et al. |
| 2003/0195589 A1 | 10/2003 | Von Arx et al. |
| 2004/0027306 A1 | 2/2004 | Amundson et al. |
| 2004/0046637 A1 | 3/2004 | Wesby Van Swaay |
| 2004/0060011 A1 | 3/2004 | Nitta et al. |
| 2004/0106967 A1 * | 6/2004 | Von Arx et al. ............... 607/60 |
| 2004/0123667 A1 | 7/2004 | McGrath |
| 2004/0147969 A1 | 7/2004 | Mann et al. |
| 2004/0147974 A1 | 7/2004 | Engmark et al. |
| 2004/0152953 A1 | 8/2004 | Goedeke |
| 2004/0167580 A1 | 8/2004 | Mann et al. |
| 2004/0176811 A1 | 9/2004 | Von Arx et al. |
| 2004/0215958 A1 | 10/2004 | Ellis et al. |
| 2005/0027175 A1 | 2/2005 | Yang |
| 2005/0027192 A1 | 2/2005 | Govari et al. |
| 2005/0113886 A1 | 5/2005 | Fischell et al. |
| 2005/0203583 A1 | 9/2005 | Twetan et al. |
| 2005/0203584 A1 | 9/2005 | Twetan et al. |
| 2005/0222633 A1 | 10/2005 | Edvardsson |
| 2006/0089682 A1 | 4/2006 | Kronich et al. |
| 2006/0224206 A1 | 10/2006 | Dublin |
| 2006/0247711 A1 | 11/2006 | Verhoef et al. |
| 2006/0247712 A1 | 11/2006 | Fuller et al. |
| 2007/0142829 A1 | 6/2007 | Ahn |
| 2007/0179554 A1 | 8/2007 | Iyer et al. |
| 2007/0222697 A1 | 9/2007 | Caimi et al. |
| 2007/0260294 A1 | 11/2007 | Schulman et al. |
| 2007/0288065 A1 | 12/2007 | Christman et al. |
| 2007/0288066 A1 | 12/2007 | Christman et al. |
| 2008/0021522 A1 | 1/2008 | Verhoef et al. |
| 2008/0039898 A1 | 2/2008 | Lim et al. |
| 2009/0192574 A1 | 7/2009 | Von Arx et al. |
| 2010/0204759 A1 | 8/2010 | Christman et al. |

FOREIGN PATENT DOCUMENTS

| | | |
|---|---|---|
| EP | 1393672 A1 | 3/2004 |
| EP | 1537895 A1 | 6/2005 |
| EP | 1362614 B1 | 3/2008 |
| WO | WO-98/48895 A1 | 11/1998 |
| WO | WO-00/62664 A1 | 10/2000 |
| WO | WO-01/80731 A1 | 11/2001 |
| WO | WO-01/91428 A2 | 11/2001 |
| WO | WO-02/31909 A1 | 4/2002 |
| WO | WO-02/089667 A1 | 11/2002 |
| WO | WO-03/053515 A1 | 7/2003 |
| WO | WO-2004/066834 A1 | 8/2004 |
| WO | WO-2005/123186 | 12/2005 |
| WO | WO-2006/060750 A1 | 6/2006 |
| WO | WO-2006/131302 A1 | 12/2006 |

OTHER PUBLICATIONS

"U.S. Appl. No. 09/798,249, Notice of Allowance mailed Oct. 21, 2003", 5 pgs.

"U.S. Appl. No. 09/798,249, Response filed Jul. 28, 2003 to Non Final Office Action mailed Mar. 28, 2003", 8 pgs.

"U.S. Appl. No. 09/921,653, Notice of Allowance mailed May 7, 2002", 6 pgs.

"U.S. Appl. No. 10/252,494, Non-Final Office Action mailed Jan. 30, 2003", 4 pgs.

"U.S. Appl. No. 10/252,494, Notice of Allowance mailed Mar. 25, 2003", 5 pgs.

"U.S. Appl. No. 10/252,494, Response filed Mar. 5, 2003 to Non Final Office Action mailed Jan. 30, 2003", 6 pgs.

"U.S. Appl. No. 10/634,233, Notice of Allowance mailed Jun. 16, 2004", 6 pgs.

"U.S. Appl. No. 10/800,596, Amendment and Response filed Jun. 7, 2007 to Final Office Action mailed Mar. 7, 2007", 8 pgs.

"U.S. Appl. No. 10/800,596, Final Office Action mailed Dec. 4, 2007", 4 pgs.

"U.S. Appl. No. 10/800,596, Final Office Action mailed Mar. 7, 2007", 7 pgs.

"U.S. Appl. No. 10/800,596, Non-Final Office Action mailed Mar. 3, 2008", 9 pgs.

"U.S. Appl. No. 10/800,596, Non-Final Office Action mailed Jun. 28, 2007", 6 pgs.

"U.S. Appl. No. 10/800,596, Notice of Allowance mailed Sep. 17, 2008", 4 pgs.

"U.S. Appl. No. 10/800,596, Response filed Feb. 4, 2008 to Final Office Action mailed Dec. 4, 2007", 6 pgs.

"U.S. Appl. No. 10/800,596, Response filed Jun. 3, 2008 to Non-Final Office Action mailed Mar. 3, 2008", 8 pgs.

"U.S. Appl. No. 10/800,596, Response filed Sep. 28, 2007 to Non-Final Office Action mailed Jun. 28, 2007", 8 pgs.

"U.S. Appl. No. 11/423,254, Non-Final Office Action mailed Jul. 28, 2009", 10 pgs.

"U.S. Appl. No. 11/423,254, Response filed Apr. 30, 2009 to Restriction Requirement filed Mar. 31, 2009", 11 pgs.

"U.S. Appl. No. 11/423,254, Response filed Oct. 28, 2009 to Non Final Office Action mailed Jul. 28, 2009", 14 pgs.

"U.S. Appl. No. 11/423,254, Restriction Requirement mailed Mar. 31, 2009", 9 pgs.

"U.S. Appl. No. 11/423,262 Response filed Mar. 24, 2009 to Non Final Office Action mailed Dec. 24, 2008", 9 pgs.

"U.S. Appl. No. 11/423,262, Non-Final Office Action mailed Dec. 24, 2008", 9 pgs.

"U.S. Appl. No. 11/423,262, Notice of Allowance mailed Jun. 23, 2009", 7 pgs.

Karacolak, T., et al., "Design of a Dual-Band Impantable Antenna and Development of Skin Mimicking Gels for Continuous Glucose Monitoring", *IEEE Transactions on Microwave Theory and Techniques*, 56(4), (Apr. 2008), 1001-1008.

"U.S. Appl. No. 11/423,254, Notice of Allowance mailed Dec. 31, 2009", 7 pgs.

"U.S. Appl. No. 12/762,086, Non Final Office Action Mailed Jan. 30, 2012", 11 pgs.

* cited by examiner

MULTI-ANTENNA FOR AN IMPLANTABLE MEDICAL DEVICE

CROSS REFERENCE TO RELATED APPLICATION

This application is a continuation of U.S. application Ser. No. 11/423,262, filed Jun. 9, 2006, now issued as U.S. Pat. No. 7,613,522, which is hereby incorporated by reference in its entirety.

TECHNICAL FIELD

This disclosure relates to implantable medical devices, particularly systems for enabling telemetry in implantable medical devices.

BACKGROUND

Certain implantable medical devices (IMDs) have the capability to communicate data with an external communication, monitoring or control device via a telemetry link. Examples include cardiac rhythm management devices such as pacemakers and implantable cardioverters/defibrillators, and neurostimulators. Data typically transmitted between an external device and an IMD includes operating parameters, stimulus and sensing modes and physiological data.

In previous telemetry systems, the IMD and the external device communicated by generating and sensing a modulated magnetic field between the devices, with the antennas of the respective devices inductively coupled together and adapted for near-field communication. The external device included a wand having an antenna, and the wand had to be in close proximity to the IMD, typically within a few inches, in order for communications to take place.

Thus, there is a need for systems for enabling longer distance, higher data rate telemetry in implantable medical devices.

SUMMARY

Disclosed herein, among other things, is an implantable medical device having radio-frequency telemetry capabilities. The device includes a housing and electronic circuitry contained within the housing. The device also includes two or more antennas connected to the electronic circuitry. According to various embodiments, the antennas and circuitry are adapted to facilitate transmission and reception of modulated radio-frequency energy at one or more specified carrier frequencies. Individual antenna element geometries are sized to optimize individual antennas each for a different range of operating frequencies and/or termination media, according to various embodiments. The antenna is adapted for far-field communication, according to various embodiments.

A device embodiment includes a housing and electronic circuitry contained within the housing. The device also includes an array of antennas connected to the electronic circuitry. According to various embodiments, the array and circuitry are adapted to facilitate transmission and reception of modulated radio-frequency energy at one or more specified carrier frequencies. Individual antenna elements in the array are connected in a mutually exclusive manner to electronic circuitry having a single transmit/receive antenna port using a switch, according to various embodiments. The antenna is adapted for far-field communication, according to various embodiments.

One aspect of this disclosure relates to a method for making an IMD having radio-frequency telemetry capabilities. According to various embodiments, the method includes forming an antenna assembly, including forming an array of antennas adapted to facilitate transmission and reception of modulated radio-frequency energy at one or more specified carrier frequencies. The method embodiment also includes installing the antenna assembly in an implantable medical device. The method embodiment further includes connecting the antenna assembly to electronic circuitry within the implantable medical device.

This Summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

DETAILED DESCRIPTION

The following detailed description refers to the accompanying drawings which show, by way of illustration, specific aspects and embodiments in which the present invention may be practiced. These embodiments are described in sufficient detail to enable those skilled in the art to practice the invention. Other embodiments may be utilized and structural, logical, and electrical changes may be made without departing from the scope of the present invention.

The present disclosure provides a system for enabling radio-frequency telemetry in implantable medical devices (IMD). Examples of IMDs include, but are not limited to: cardiac rhythm management devices such as pacemakers and implantable cardioverters/defibrillators; passive implantable monitoring devices; peripheral devices such as weight scales or blood pressure monitors; and neurostimulators. Multiple antennas, or antenna arrays, for use with an IMD are provided. Individual antenna elements in the array are connected in a mutually exclusive manner to electronic circuitry having a single transmit/receive antenna port using a switch, according to various embodiments. Additionally, antenna configurations having switched diversity, phased array, or full diversity can be provided. The present disclosure provides: greater range for reliable, high-speed communication with an IMD; more uniform radiation performance, independent of device orientation or surroundings; improved tuning for specific media; and consistent operation across a broad range of frequencies and dielectric terminations.

Implantable Medical Devices

Figure 1:
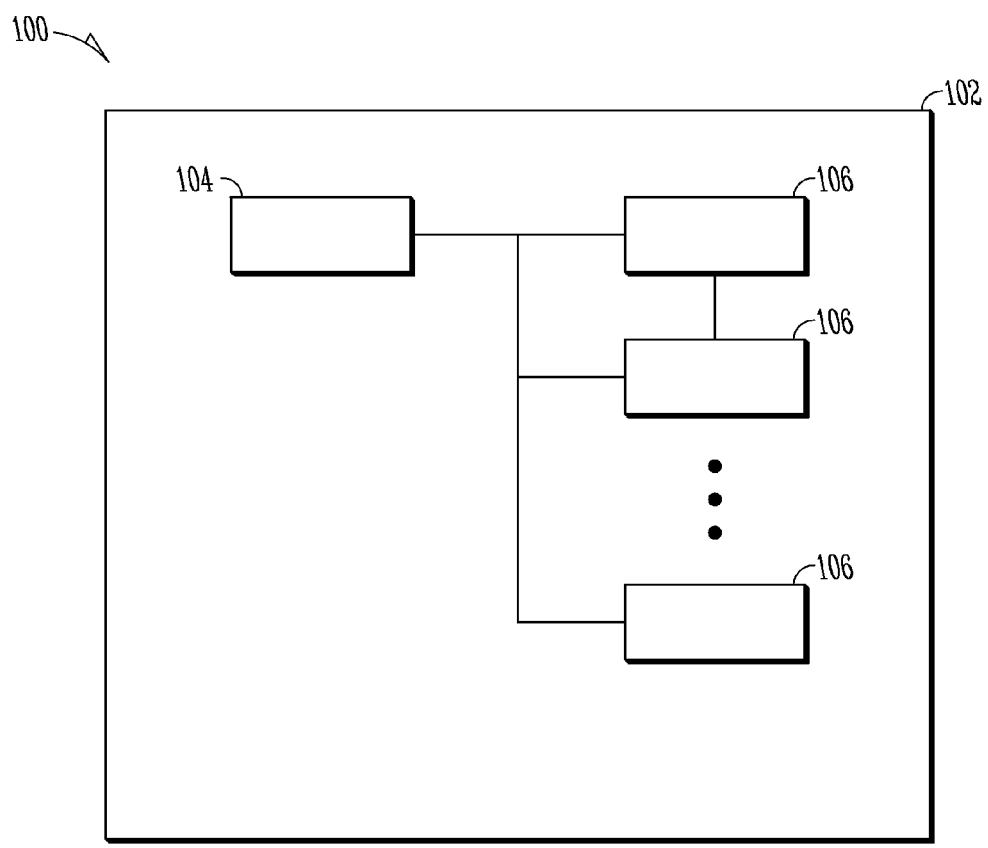
FIG. 1 illustrates a block diagram of an implantable medical device having multiple radio-frequency telemetry antennas, according to one embodiment.

FIG. 1 illustrates a block diagram of an implantable medical device having multiple radio-frequency telemetry antennas, according to one embodiment. The device 100 includes a housing 102 and electronic circuitry 104 contained within the housing. The device also includes an array of antennas 106 connected to the electronic circuitry 104. According to various embodiments, the array 106 and circuitry 104 are adapted to facilitate far-field transmission and reception of modulated radio-frequency energy at one or more specified carrier frequencies. Individual antenna elements in the array are connected simultaneously or in a mutually exclusive manner to electronic circuitry having a single transmit/receive antenna port using a switch, according to various embodiments. The antennas in the array of antennas may include a variety of different antenna element geometries, such as helical, loop, serpentine, inverted F, or other appropriate configuration. According to an embodiment, two or more of the antennas in the array have identical antenna element geometries. The antennas in the array may operate independently or simultaneously.

Individual antenna elements in the array are connected in a mutually exclusive manner to electronic circuitry having a single transmit/receive antenna port using a switch, according to various embodiments. This configuration has a switched diversity. The switch may include a mechanical switch or an electrical switch, according to various embodiments. The state of the switch (open or closed) can be changed to minimize an observed error rate or to restore communication upon loss of radio frequency communication (using logic to sequence a pre-determined order of states until communication is restored), in some embodiments. According to one embodiment, the array includes a photochemically-etched metallization pattern on a planar dielectric substrate.

According to various embodiments, individual antenna elements in the array are each connected to electronic circuitry having a single transmit/receive antenna port via inline phase shifting elements, such that each antenna element transmits/receives a proportion of radio-frequency energy to the electronic circuitry with a phase shift. This configuration is considered a phased array. In one embodiment, the phase shift for each antenna element in the array can be fixed to establish a desired shape of a transmit/receive spatial pattern. The phase shift for each antenna element in the array can also be variable and controlled by logic to dynamically alter a shape of a transmit/receive spatial pattern, according to an embodiment. In the variable phase shift embodiment, logic can be used to alter the relative phase shift of each antenna element, and scanning is performed according to a fixed sequence of phases. Logic can also be used to alter relative phases of each antenna element taking into account an observed bit, frame or packet error rate, and selecting the state, or beam-steering, to minimize an observed error rate.

Individual antenna elements in the array are each connected to electronic circuitry having multiple transmit/receive antenna ports, such that each antenna element is capable of operating independently, according to various embodiments. This configuration has full diversity. According to one embodiment, each antenna element in the array is switched by logic according to a fixed sequence of states. According to another embodiment, each antenna element in the array is phase-shifted by logic according to a fixed sequence of states. According to a further embodiment, each antenna element in the array is switched by logic to minimize an observed error rate. Each antenna element in the array is phase-shifted by logic to minimize an observed error rate, according to an embodiment.

A device embodiment includes a housing and electronic circuitry contained within the housing. The device also includes two or more antennas connected to the electronic circuitry. According to various embodiments, the antennas and circuitry are adapted to facilitate far-field transmission and reception of modulated radio-frequency energy at one or more specified carrier frequencies. In various embodiments, the specified carrier frequency includes frequencies within the range from 300 MHz to 1 GHz. The antenna can be scaled for other frequency ranges, in various embodiments. For example, frequencies in S-band (ranging from 2.0-4.0 GHz) or frequencies in X-band (ranging from 8.0-12.0 GHz) can be used as the carrier frequency, according to various embodiments.

The individual antennas may have the same or different geometries, according to various embodiments. Individual antenna element geometries are sized to optimize individual antennas each for a different range of operating frequencies, according to various embodiments. For example, an implantable medical device may require operation in multiple independent frequency bands. According to an embodiment, individual antenna element geometries are sized to optimize individual antennas each for a different termination medium. Examples of termination media include air, muscle tissue, and fatty tissue.

Figure 2A:
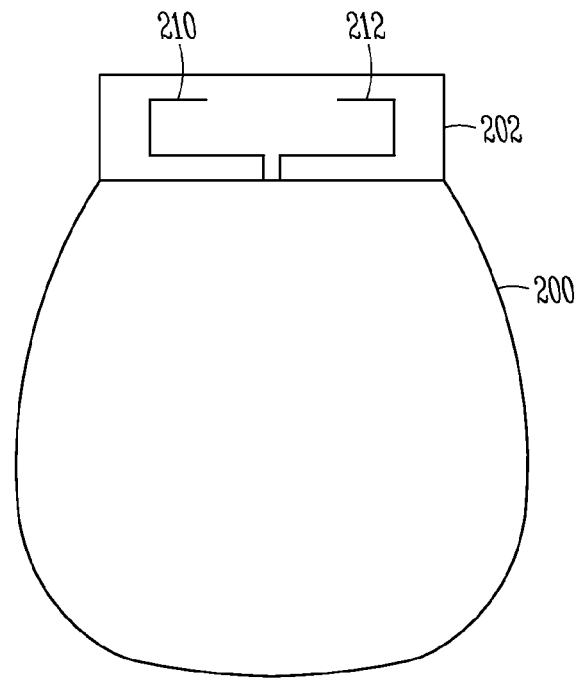
FIG. 2A illustrates a side view of an implantable medical device having multiple radio-frequency telemetry antennas in a header, according to one embodiment.
Figure 2B:
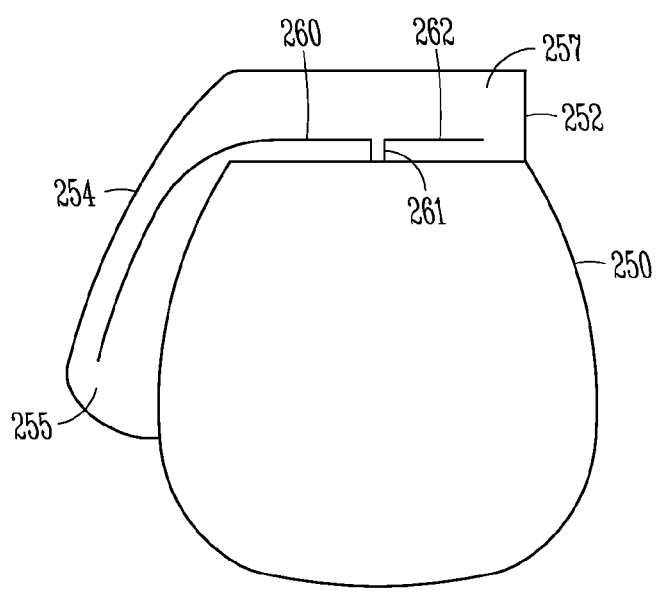
FIG. 2B illustrates a side view of an implantable medical device having radio-frequency telemetry antennas in a header and in a compartment, according to one embodiment.

FIGS. 2A and 2B depict dipole antenna configurations for implantable medical devices. FIG. 2A illustrates a side view of an implantable medical device having multiple radio-frequency telemetry antennas in a header, according to one embodiment. The depicted device 200 has a first antenna 210 and a second antenna 212 in a header 202. The header can be adapted to connect to one or more leads having one or more electrodes adapted to deliver electrical therapy. FIG. 2B illustrates a side view of an implantable medical device having radio-frequency telemetry antennas in a header and in a compartment, according to one embodiment. The device 250 has a first antenna 262 residing entirely in a header 252 and a second antenna 260 having at least a portion in a compartment 254 on the side of the device housing. Other numbers of antennas and antenna configuration are within the scope of the disclosure.

According to one embodiment, the compartment can be partially or completely comprised of a dielectric material 255. The dielectric material 255 in the compartment can be the same or different than the dielectric material 257 in the device header. According to an embodiment, the dielectric material 255 in the compartment has a higher relative dielectric constant to facilitate more efficient coupling of radiation into a surrounding implant medium of high dielectric constant material, such as when the device is implanted in muscle tissue. According to various embodiments, the dielectric material can include a sleeve of alumina, a sleeve of a ceramic, or a high-dielectric constant liquid in a sleeve surrounding the antenna. The dielectric materials need not be high-dielectric constant materials, according to various embodiments. In various embodiments, the dielectric material surrounding the antenna may include an overmold dielectric material, medical adhesive backfill dielectric material, or circuit board dielectric material. When discussing dielectric material, the dielectric constant "k" is used to describe the relative permittivity of the material. For the purposes of this disclosure, a material with a dielectric constant above 4.0 (the dielectric constant of silicon dioxide) is considered a high dielectric constant material.

The device also includes a feed conductor 261 adapted to provide an electrical connection between the electronic circuitry and the antennas, according to various embodiments. In addition, the feed conductor 261 can be adapted to connect to one of the antennas at a point along the antenna selected for optimal transmitting and receiving of radio-frequency energy at a specified frequency, or over a specified range of frequencies.

The device also includes a return structure 417 (FIG. 4) attached to one of the antennas, the return structure 417 (FIG. 4) adapted to provide a conductive return path connected to the electronic circuitry or the device housing, according to various embodiments. In one embodiment, the return structure 417 (FIG. 4) can be connected only to the antenna to provide a capacitive return path through reactive coupling to a nearby conductive grounding structure 419 (FIG. 4) connected to the electronic circuitry or the housing. The return structure 417 (FIG. 4) can include a conductor suspended in a dielectric a predetermined distance from the device housing to prevent high-voltage arc-over during therapy delivery, and positioned to maximize the reactive coupling of the radio frequency energy from the return structure 417 (FIG. 4) to the housing forming a low impedance path over a selected range of frequencies. The feed and return structures, which provide electrical connection between the antennas and the electronic circuitry in the housing, may be comprised of linear segments, plates, or other suitable geometry. The device also includes a frequency selective isolation transformer adapted to isolate the feed conductor and the return structure from therapy voltages, according to various embodiments. According to one embodiment, the device also includes a switch adapted to isolate the feed conductor and the return structure from therapy voltages.

According to various embodiments, the compartment 254 includes a first dielectric material 255 and the header 252 includes a second dielectric material 257. The first and second dielectric material 255, 257 may be the same or a different material. According to various embodiments, the first dielectric material 255 can include a sleeve of alumina, a sleeve of a ceramic, or a high-dielectric constant liquid in a sleeve surrounding the antennas. The dielectric materials need not be high-dielectric constant materials, according to various embodiments. In various embodiments, the dielectric material surrounding the antenna may include an overmold dielectric material, medical adhesive backfill dielectric material, or circuit board dielectric material.

The antennas can be made of formed, rolled, stamped or cast metal or conductive composite material and may be a wire, band/ribbon, or hollow structure. The antenna housing or compartment can be formed, molded, machined or cast plastic or composite material. The antennas and their housing can be mounted internally or externally in either an implantable device or an external communication device, such as the programmer of FIG. 5, below. The antenna structure for each antenna can be end-fed in the header or at the base, or any other penetration through the device housing. The antennas can be fed at their end or along their length, and can contain an open or shunt stub termination to the housing or other ground connection. The return path can be capacitive or conductive, and the antennas may include features to enhance capacitive coupling. The antennas can be fed by a waveguiding structure and this feed may include high-voltage isolation.

Figure 3A:
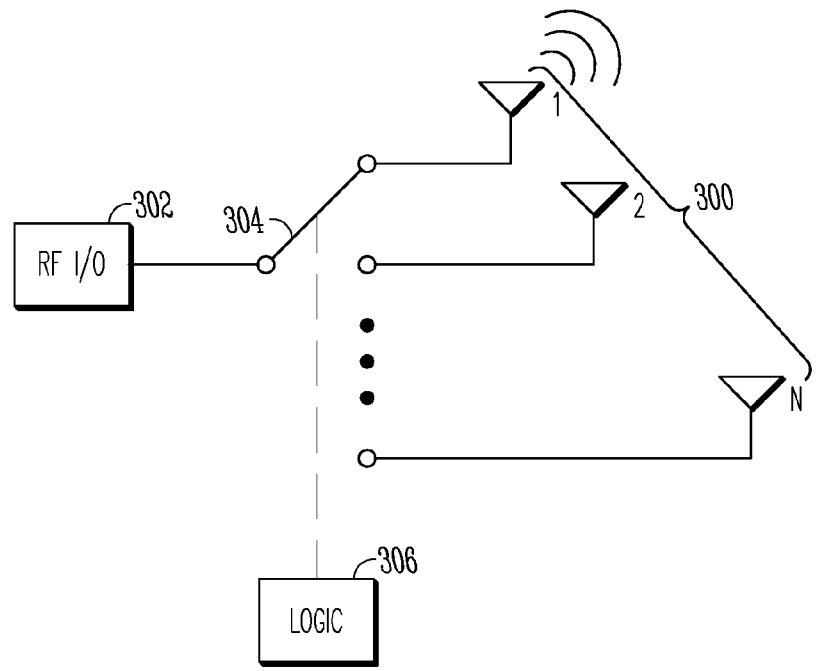
FIG. 3A illustrates a radio frequency antenna array for an implantable medical device having switched diversity, according to one embodiment.

FIG. 3A illustrates a radio frequency antenna array for an implantable medical device having switched diversity, according to one embodiment. The array 300 includes N discrete antennas, where N is greater than or equal to two. The antenna array may include one or more patch, ribbon, wire, helical, or inverted F type individual antennas. Other types of antennas may be used in the antenna array without departing from the scope of the disclosure. Radio frequency transceiver circuitry 302 is connected to the array via a switch 304, which may be mechanical or electrical. The switch 304 is controlled by logic 306 to determine which of the antennas in the array is connected to the transceiver circuitry 302. Logic 306 may control the switch 304 based on a programmed sequence, a predetermined order, or a closed loop system based on observed environmental conditions.

Figure 3B:
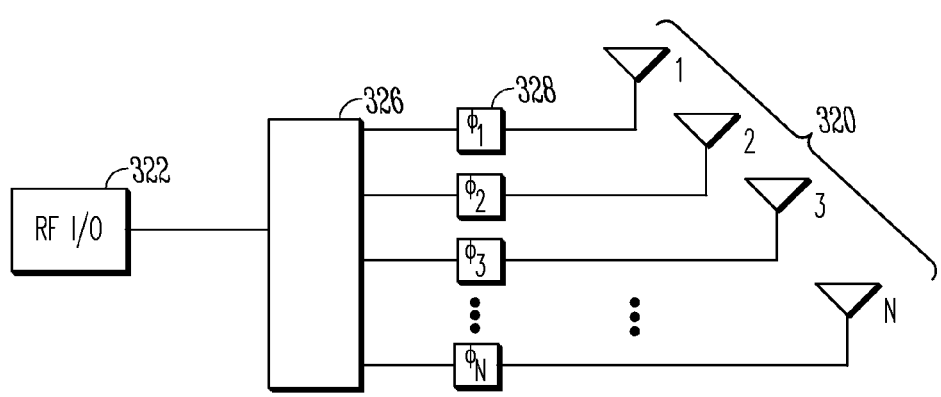
FIG. 3B illustrates a radio frequency antenna phased array for an implantable medical device, according to one embodiment.

FIG. 3B illustrates a radio frequency antenna phased array for an implantable medical device, according to one embodiment. The array 320 includes N discrete antennas, where N is greater than or equal to two. The antenna array may include one or more patch, ribbon, wire, helical, or inverted F type individual antennas. Other types of antennas may be used in the antenna array without departing from the scope of the disclosure. Radio frequency transceiver circuitry 322 is connected to the array via logic 326 according to phase feeds 328. Variable phase feeds to each antenna in the array provide for more than one antenna to be actively transmitting or receiving at the same time, which enables the beam-steering discussed above. According to an embodiment, the logic alters relative phase shift of at least one antenna element to restore communication upon loss of radio frequency communication. The array includes a photochemically-etched metallization pattern on a planar dielectric substrate, according to an embodiment.

Figure 3C:
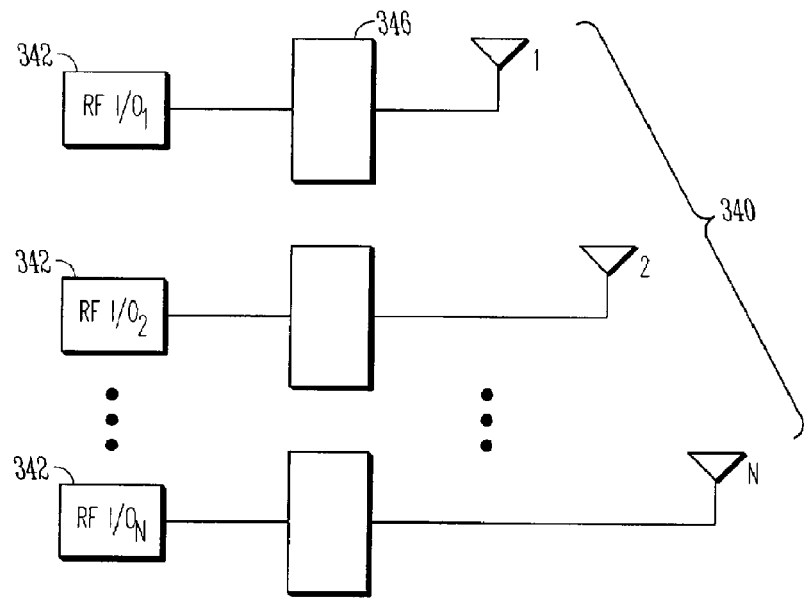
FIG. 3C illustrates a radio frequency antenna array for an implantable medical device having full diversity, according to one embodiment.

FIG. 3C illustrates a radio frequency antenna array for an implantable medical device having full diversity, according to one embodiment. The array 340 includes N discrete antennas, where N is greater than or equal to two. The antenna array may include one or more patch, ribbon, wire, helical, or inverted F type individual antennas. Other types of antennas may be used in the antenna array without departing from the scope of the disclosure. Each antenna has dedicated radio-frequency transceiver circuitry 342 connected to the array via logic 346. In this embodiment all antennas in the array can be actively transmitting or receiving at the same time. According to an embodiment, at least one antenna element in the array is switched by logic to restore communication upon loss of radio frequency communication. The array includes a photochemically-etched metallization pattern on a planar dielectric substrate, according to an embodiment.

System for Enabling Radio-Frequency Telemetry in IMD

Figure 4:
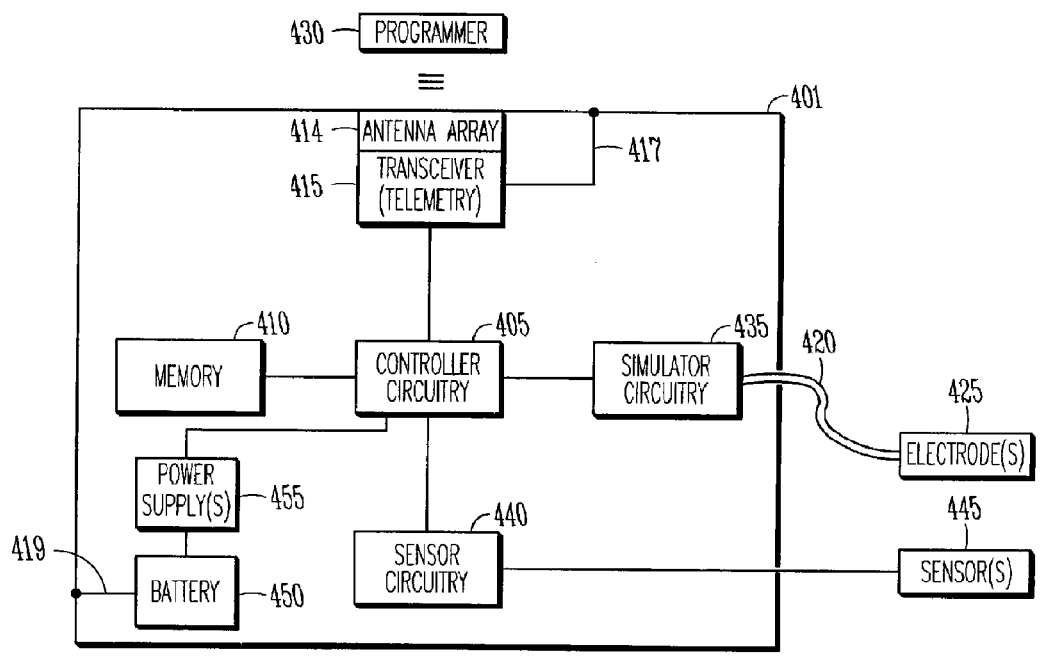
FIG. 4 illustrates a block diagram of a system with an IMD having radio-frequency telemetry capabilities, according to one embodiment.

FIG. 4 illustrates a block diagram of a system with an IMD having radio-frequency telemetry capabilities, according to one embodiment. The system includes an IMD 401, an electrical lead 420 coupled to the IMD 401, and at least one electrode 425. The IMD includes a controller circuit 405, a memory circuit 410, an antenna array 414, a telemetry circuit 415, and a stimulation circuit 435. At least one battery 450 connects to one or more power supplies 455 to provide electrical power to the device. The depicted power supply 455 is connected to the controller circuit 405. The controller circuit 405 is operable on instructions stored in the memory circuit to deliver stimulation therapy. Therapy is delivered by the stimulation circuit 435 through the lead 420 and the electrode(s) 425 to stimulate the myocardia or a neural target. Other stimulation targets and other types of therapy, such as drug delivery, are within the scope of this disclosure. The telemetry circuit 415 and antenna array 414 (such as the antenna array depicted in FIG. 1) allow communication with an external communication, monitoring or control device, such as programmer 430. Other examples of external devices include a bedside monitor or hand-held programming or monitoring device. The programmer 430 can be used to adjust the programmed therapy provided by the IMD 401, and the IMD can report device data (such as battery and lead resistance) and therapy data (such as sense and stimulation data) to the programmer using radio telemetry, for example. According to various embodiments, the IMD 401 senses one or more physiological parameters and delivers stimulation therapy. The illustrated system also includes sensor circuitry 440 that is coupled to at least one sensor 445. The controller circuit 405 processes sensor data from the sensor circuitry and delivers a therapy responsive to the sensor data.

Figure 5:
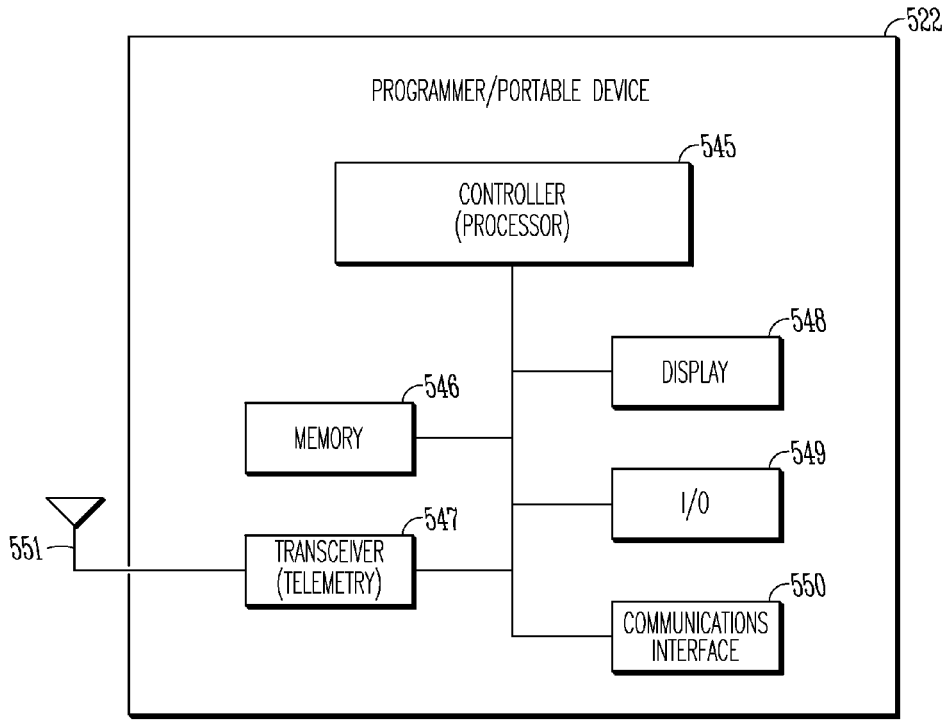
FIG. 5 illustrates a block diagram of an external communication, monitoring or control device such as illustrated in the system of FIG. 4 or other external device to communicate with the IMD(s), according to one embodiment.

FIG. 5 illustrates a block diagram of an external communication, monitoring or control device such as illustrated in the system of FIG. 4 or other external device to communicate with the IMD(s), according to one embodiment. Examples of external communication, monitoring or control devices include programmers, bedside monitors, hand-held programming or monitoring devices, and Personal Digital Assistants (PDAs) or personal laptop and desktop computers in an Advanced Patient Management (APM) system. The illustrated device 522 includes controller circuitry 545 and a memory 546. The controller circuitry 545 is capable of being implemented using hardware, software, and combinations of hardware and software. For example, according to various embodiments, the controller circuitry 545 includes a processor to perform instructions embedded in the memory 546 to perform a number of functions, including communicating data and/or programming instructions to the implantable devices. The illustrated device 522 further includes a transceiver 547 and associated circuitry for use to communicate with an implantable device. Various embodiments have wireless communication capabilities. For example, various embodiments of the transceiver 547 and associated circuitry are connected to an antenna 551 or an antenna array to wirelessly communicate with an implantable device. The illustrated device 522 further includes a display 548, input/output (I/O) devices 549 such as a keyboard or mouse/pointer, and a communications interface 550 for use to communicate with other devices, such as over a communication network.

Method for Enabling Radio-Frequency Telemetry in IMD

Figure 6:
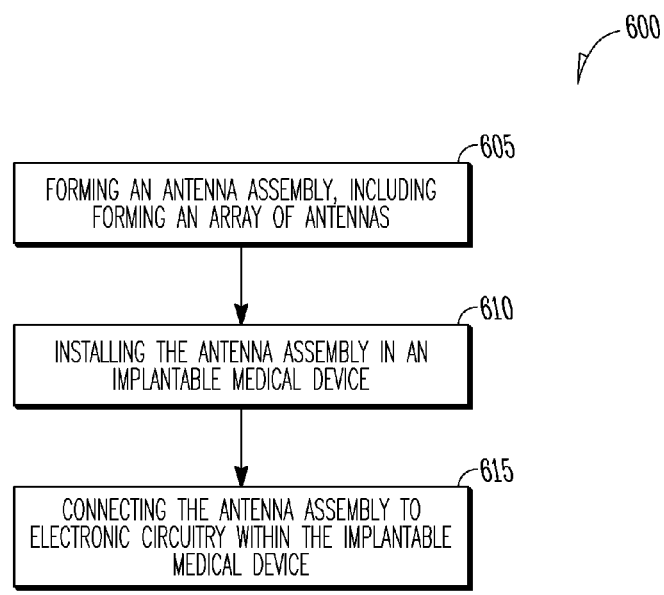
FIG. 6 illustrates a flow diagram of a method for making an IMD having multiple radio-frequency telemetry antennas, according to one embodiment.

FIG. 6 illustrates a flow diagram of a method for making an IMD having multiple radio-frequency telemetry antennas, according to one embodiment. According to various embodiments, the method 600 includes forming an antenna assembly, including forming an array of antennas adapted to facilitate transmission and reception of modulated radio-frequency energy at one or more specified carrier frequencies, at 605. The method embodiment also includes installing the antenna assembly in an implantable medical device, at 610. The method embodiment further includes connecting the antenna assembly to electronic circuitry within the implantable medical device, at 615.

The above method is not limited to antenna arrays, and can be altered to include forming two or more antennas in the antenna assembly, in various embodiments. According to one embodiment, forming the antenna assembly includes surrounding the antenna array with a dielectric material. According to another embodiment, the antenna array is surrounded with a dielectric material after installing the antenna assembly in the IMD. Surrounding the antenna array with a dielectric material may include overmolding the antenna array, backfilling with a medical adhesive, or use of other types of dielectric materials such as circuit board material, human tissue, and/or high-dielectric constant materials. Installing the antenna assembly in an implantable medical device includes placing the antenna array in a device header, according to various embodiments. According to various embodiments, the antennas and circuitry are adapted to facilitate far-field transmission and reception of modulated radio-frequency energy at a specified carrier frequency.

According to various embodiments, at least one antenna in the array can be formed using stamped metal, rolled metal, formed metal or cast metal. At least one antenna in the array can also be formed using conductive composite material, according to an embodiment. According to various embodiments, forming an array of antennas includes forming at least one antenna with a helical portion. The helical portion of the antenna includes a metal wire wound around a bobbin, according to an embodiment. Forming an array of antennas includes surrounding at least one antenna with dielectric-embedded passive (non-driven) elements adapted to change shape of a transmit and receive spatial pattern, according to an embodiment. These passive elements are also referred to as directors, and may be metallic in various embodiments. The passive elements are adapted to tune the antenna(s) for more efficient transmission and receipt of energy over a specified range of frequencies. According to an embodiment, a patch antenna array can be formed with some passive (non-driven) elements used as directors to tune the antenna(s). A planar substrate may also be used in an embodiment, with a metallization pattern having non-driven elements and a reflector for tuning at least one antenna in the array.

One of ordinary skill in the art will understand that, the modules and other circuitry shown and described herein can be implemented using software, hardware, and combinations of software and hardware. As such, the illustrated modules and circuitry are intended to encompass software implementations, hardware implementations, and software and hardware implementations.

This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

What is claimed is:

1. An implantable medical device, comprising:
a housing;
electronic circuitry at least partially contained within the housing;
at least two antennas electrically connected to the electronic circuitry, wherein the at least two antennas and electronic circuitry are configured to wirelessly transfer information using modulated radio-frequency energy; and
wherein the at least two antennas comprise:
a first antenna configured to wirelessly transfer information at a specified first range of operating frequencies when the first antenna is substantially surrounded by a specified first medium; and
a second antenna configured to wirelessly transfer information at a specified second range of operating frequencies when the second antenna is substantially surrounded by a specified second medium different than the first medium.

2. The device of claim 1, wherein the first and second specified ranges of operating frequencies at least partially overlap.

3. The device of claim 1, wherein the specified first medium includes air.

4. The device of claim 3, wherein the specified second medium includes a tissue medium selected from a list including fatty tissue or muscle tissue.

5. The device of claim 1, wherein at least one of the at least two antennas is configured to be selectively electrically connected to the electronic circuitry.

6. The device of claim 5, wherein the electronic circuitry is configured to wirelessly transfer information using the at least one antenna exclusively, when the at least one antenna is selected.

7. The device of claim 5, wherein the electronic circuitry is configured to wirelessly transfer information using the at least one antenna simultaneously with one or more of the at least two antennas, when the at least one antenna is selected.

8. The device of claim 5, wherein the electronic circuitry is configured to detect a condition and to select at least one of the at least two antennas for use in wireless information transfer in response to the detected condition.

9. The device of claim 8, wherein the electronic circuitry includes an error rate detector, wherein the error rate detector is configured to detect a wireless information transfer error rate, and wherein the electronic circuitry is configured to select at least one of the at least two antennas for use in wireless information transfer in response to the wireless information transfer error rate detected at or in excess of a specified error rate threshold.

10. The device of claim 8, wherein the electronic circuitry is configured to detect a loss of wireless information transfer between the implantable device and at least one other device separate from the implantable device, and wherein the electronic circuitry is configured to select at least one of the at least two antennas to reestablish wireless information transfer in response to the detected loss of wireless information transfer.

* * * * *